United States Patent [19]

Fukunishi et al.

[11] Patent Number: 5,704,896
[45] Date of Patent: Jan. 6, 1998

[54] ENDOSCOPE APPARATUS WITH LENS FOR CHANGING THE INCIDENT ANGLE OF LIGHT FOR IMAGING

[75] Inventors: Souhei Fukunishi; Yumiko Okada; Tadashi Sekiguchi, all of Tokyo, Japan

[73] Assignee: Kabushiki Kaisha Toshiba, Kawasaki, Japan

[21] Appl. No.: 424,108

[22] Filed: Apr. 19, 1995

[30] Foreign Application Priority Data

Apr. 27, 1994 [JP] Japan .................................. 6-089562
Oct. 12, 1994 [JP] Japan .................................. 6-246491

[51] Int. Cl.$^6$ .................................................. A61B 1/05
[52] U.S. Cl. ........................... 600/109; 600/167; 348/65; 348/340
[58] Field of Search ............................ 600/109, 160, 600/167, 176; 359/599, 619, 625; 348/65, 71, 340

[56] References Cited

U.S. PATENT DOCUMENTS

| | | | |
|---|---|---|---|
| 4,230,941 | 10/1980 | Stauffer. | |
| 4,621,897 | 11/1986 | Bonnet | 359/619 |
| 5,081,545 | 1/1992 | Sugawara et al. | 359/625 |
| 5,329,400 | 7/1994 | Miyano | 359/674 |
| 5,430,475 | 7/1995 | Goto et al. | 348/65 |
| 5,499,138 | 3/1996 | Iba | 359/619 |

OTHER PUBLICATIONS

"Microlens for Solid-state Image Pickup Element", Abstract of Japanese Patent 6-130306, May 13, 1994.

*Primary Examiner*—Richard J. Apley
*Assistant Examiner*—John P. Leubecker
*Attorney, Agent, or Firm*—Foley & Lardner

[57] ABSTRACT

A solid-state image pickup device has a photosensitive chip and an array of microlenses arranged on the incident side of the photosensitive chip. A correction lens is arranged on the incident side of the microlens array to reduce incident angles of light entering the microlenses. The solid-state image pickup device may be incorporated in a head of an endoscope of an endoscopic apparatus to receive light from an optical system arranged in the head. The head includes a unit for changing paths of light to the microlenses to reduce incident angles of the light entering the microlenses.

20 Claims, 7 Drawing Sheets

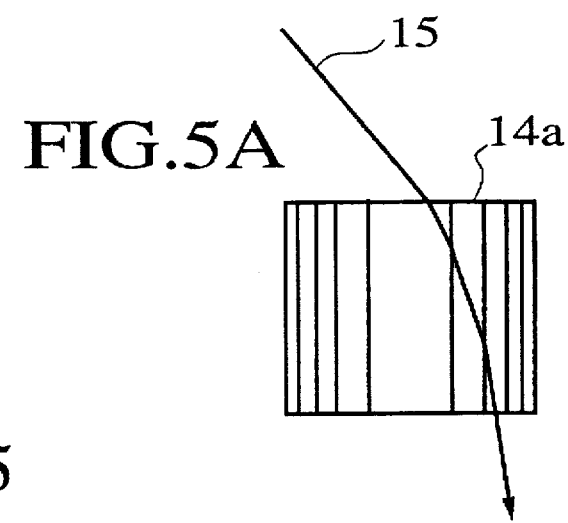
FIG.5A
FIG.5
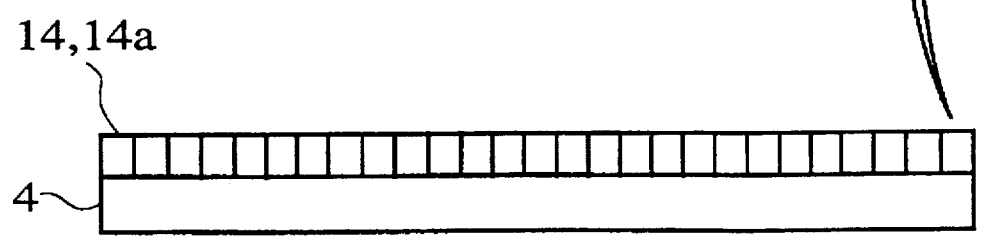

ENDOSCOPE APPARATUS WITH LENS FOR CHANGING THE INCIDENT ANGLE OF LIGHT FOR IMAGING

BACKGROUND OF THE INVENTION

The present invention relates to a solid-state image pickup device, such as a CCD (Charge Coupled Device), and an endoscopic apparatus employing the image pickup device. In particular, the present invention relates to a technique of improving the photosensitivity of the image pickup device.

Endoscopic apparatuses are widely used for medical diagnosis.

An endoscopic apparatus includes an endoscope and a main unit. The endoscope includes a tip, an insert, and a controller. The tip accommodates a solid-state image pickup device to receive light from a target part in the body.

The image pickup device is usually a CCD. Recent technology has developed a CCD that is compact but involves many pixels. The CCD has photosensitive elements such as photodiodes each having a small opening for guiding light. If the opening is too small, it will deteriorate photosensitivity. To improve the photosensitivity of each grid of photosensitive elements 3a, as shown in FIG. 1, each of the elements 3a is provided with an opening 2 to guide light. The microlens array 1 consists of microlenses 1a for condensing light onto the respective photosensitive elements 3a. Light from an object passes through the glass cover 5 and reaches the microlens array 1. The microlenses 1a condense the light onto the photosensitive elements 3a. The elements 3a convert the light into electric signals, which are transferred to an image processor.

Unlike optical systems of other image pickup apparatuses, such as television cameras and video cameras, the optical system of an endoscopic apparatus is smaller than the image pickup device because its installation space is limited. This increases an incident angle of light at an edge of the photosensitive surface of the image pickup device. A large incident angle increases the influence of reflection, which deteriorates the photosensitivity of each photosensitive element.

This raises a serious problem in endoscopic apparatuses employing a microlens array.

FIGS. 2A and 2B explain the problem of a large incident angle. Light is transmitted through a microlens 1a and enters an opening 2 of a photosensitive element. In FIG. 2A, the light 6 has a small incident angle so that it vertically enters the microlens 1a, which properly condenses the light 6 into the opening 2.

In FIG. 2B, the light 6 has a large incident angle so that it obliquely enters the microlens 1a, and part of the light 6 exceeds an allowable incident angle of the microlens 1a. Consequently, the microlens 1a condenses only a part of the light 6 into the opening 2.

Accordinyly conventional image pickup devices are incapable of entirely receiving light when the light involves a large incident angle, thereby deteriorating photosensitivity. An endoscopic apparatus employing such an image pickup device provides dark images that are insufficient for diagnostic use.

SUMMARY OF THE INVENTION

An object of the present invention is to provide a solid-state image pickup device having improved photosensitivity, and an endoscopic apparatus employing the image pickup device.

In order to accomplish the object, the present invention provides a solid-state image pickup device having a photosensitive chip including a grid of photosensitive elements; a microlens array arranged on the incident side of the photosensitive chip and including microlenses for condensing incident light onto the photosensitive elements and a correction lens arranged on the incident side of the microlens array, to reduce incident angles of light to the microlenses.

This image pickup device is capable of vertically guiding light toward the photosensitive elements, thereby improving photosensitivity.

The correction lens may be a Fresnel lens that is thin and has a saw-toothed sectional shape.

The present invention also provides an endoscopic apparatus having a head accommodating the solid-state image pickup device.

This endoscopic apparatus is capable of providing a bright image. Due to good photosensitivity, the apparatus requires no electrical processes and involves low noise.

The present invention also provides an endoscopic apparatus. The apparatus includes an endoscope comprising a head. The head accommodates an optical system having an object lens having a center axis parallel to the axis of the endoscope; a photosensitive unit having microlenses and a photosensitive chip having photosensitive elements the microlenses condensing light from the optical system onto the respective photosensitive elements; and a unit for changing paths of light to the microlenses, to reduce incident angles of the light to the microlenses.

The present invention changes paths of light that obliquely enter the photosensitive unit from the optical system toward the center axis of the photosensitive unit, depending on the incident angles of the light, to thereby secure photosensitivity. This is particularly advantageous in a solid-state image pickup device employing microlenses that are easily affected by oblique light. This effect of the present invention helps to reduce the sizes of lenses in an optical system and thus to achieve a compact endoscopic apparatus.

The solid-state image pickup device in the endoscope of the present invention may be arranged such that the photosensitive surface thereof is oriented in parallel with the axis of the endoscope. In this case, the image pickup device is provided with a prism. The prism is arranged such that an emission surface thereof faces the photosensitive surface of the image pickup device. The emission surface of the prism may be curved to serve as a lens. This configuration simplifies the structure of the head of the endoscope compared with a combination of a prism and a plano-convex lens.

The photosensitive surface of the image pickup device may have a combination of a plano-convex lens and a glass cover having a curved incident surface. This configuration expands the degree of freedom of designing compared with a structure employing a single plano-convex lens.

The nature, principle and utility of the invention will become more apparent from the following detailed description when read in conjunction with the accompanying drawings.

BRIEF DESCRIPTION OF THE DRAWINGS

FIGS. 5 and 5A are sectional views showing a solid-state image pickup device according to a third embodiment of the present invention;

DESCRIPTION OF THE PREFERRED EMBODIMENTS

Figure 1:
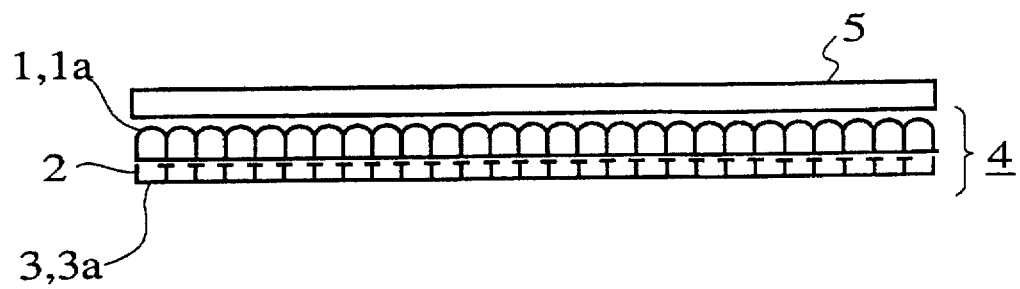
FIG. 1 is a sectional view showing a conventional solid-state image pickup device.
Figure 3:
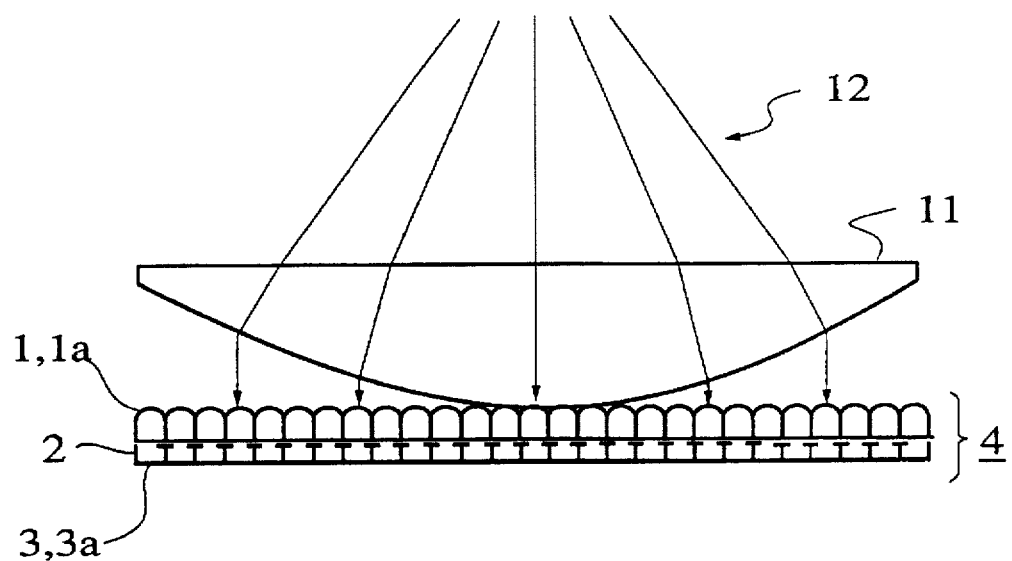
FIG. 3 is a sectional view showing a solid-state image pickup device according to a first embodiment of the present invention.

Various embodiments of the present invention will be described with reference to the accompanying drawings.
First Embodiment FIG. 3 is a sectional view showing a solid-state image pickup device. The image pickup device has a plano-convex lens 11 instead of the glass cover 5 of the prior art of FIG. 1. The plano-convex lens 11 has a flat incident surface and a convex emission surface. A photosensitive unit 4 of this embodiment is the same as that of the prior art of FIG. 1.

Figure 2A:
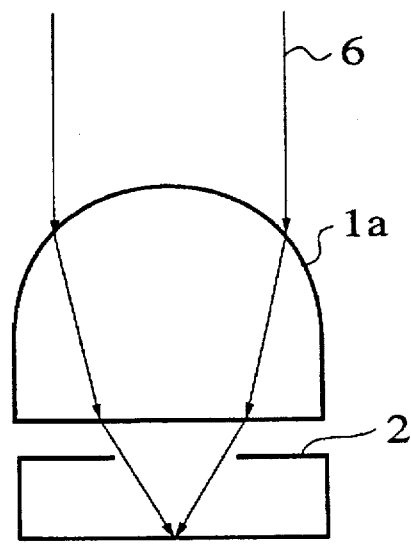
FIGS. 2A and 2B explain the incident angles and paths of light.
Figure 2B:
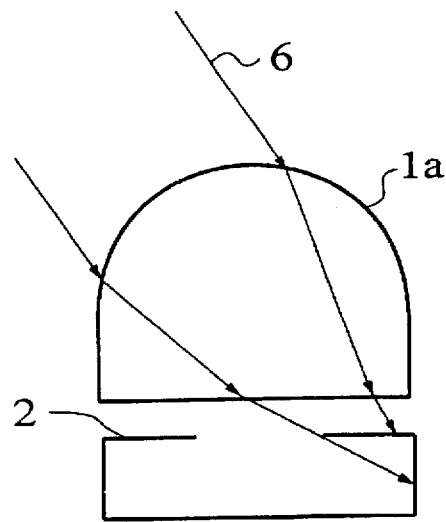
Figure 4:
FIG. 4 is a sectional view showing a solid-state image pickup device according to a second embodiment of the present invention.
Figure 6A:
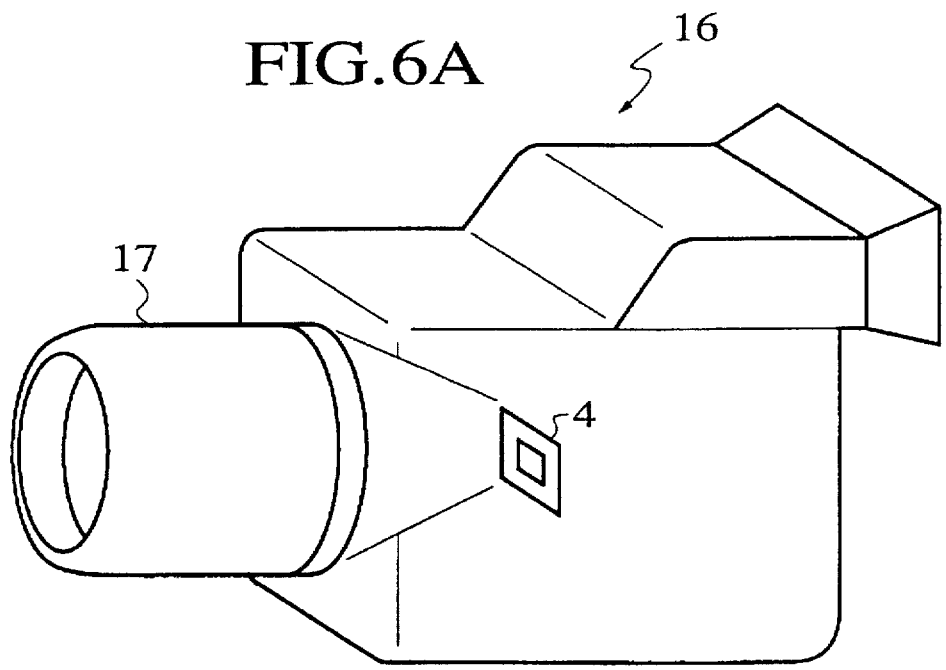
FIGS. 6A and 6B show a solid-state image pickup device according to a fourth embodiment of the present invention.

When incident light 12 is oblique with respect to the flat surface of the lens 11, it is refracted by the lens 11 at a proper refractive index and is substantially vertically guided to the photosensitive unit 4. Unlike the prior art of FIG. 2B, the light 12 properly enters the openings 2. This results in improving photosensitivity.
Second Embodiment FIG. 4 is a sectional view showing a solid-state image pickup device according to the second embodiment of the present invention. This embodiment employs a Fresnel lens 13 instead of the plano-convex lens 11 of the first embodiment. The Fresnel lens 13 has a flat incident surface and a saw-toothed convex emission surface. Similar to the first embodiment, the second embodiment is capable of substantially vertically guiding incident light to a photosensitive unit 4. The saw-toothed convex surface helps to thin the lens 13.
Third Embodiment FIG. 5 shows a solid-state image pickup device according to the third embodiment of the present invention. This embodiment employs an array 14 of rod lenses 14a arranged on a flat surface to make incident light vertical. FIG. 5A shows one of the rod lenses 14a. The rod lens 14a is formed by laminating different materials one upon another to gradually inwardly refract incident light 15. Similar to the first and second embodiments the third embodiment is capable of substantially vertically guiding incident light to a photosensitive unit 4, to improve photosensitivity.
Fourth Embodiment FIG. 6A shows a camera employing an optical system larger than a solid-state image pickup device. At an edge of a photosensitive unit 4 of the image pickup device in the camera 16, light forms a large incident angle. This incident angle is opposite to that of FIG. 2B because the optical system 17 is larger than the image pickup device.

Figure 6B:
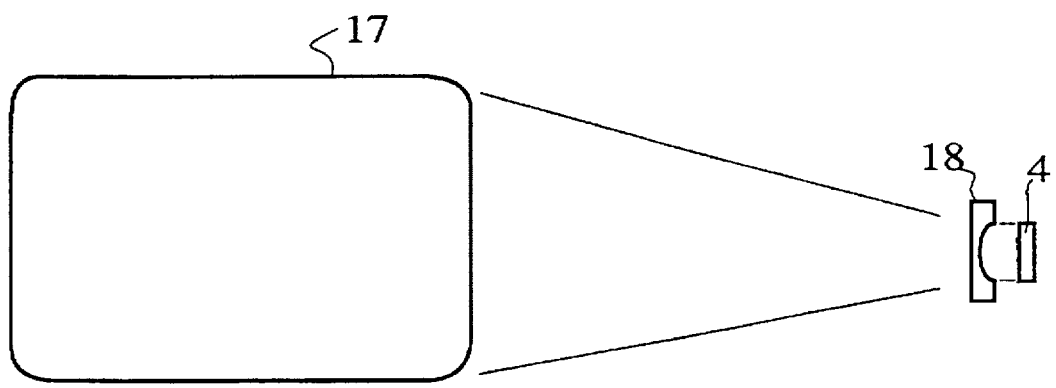

To improve photosensitivity at the periphery of the photosensitive unit 4, the fourth embodiment employs, instead of a plano-convex lens, a plano-concave lens 18 as shown in FIG. 6B.

Any one of the solid-state image pickup devices of the first to fourth embodiments may be installed in an endoscopic apparatus to receive light from an optical system. The image pickup devices of these embodiments achieve improved photosensitivity to provide bright images that are useful for diagnosis.

Figure 7:
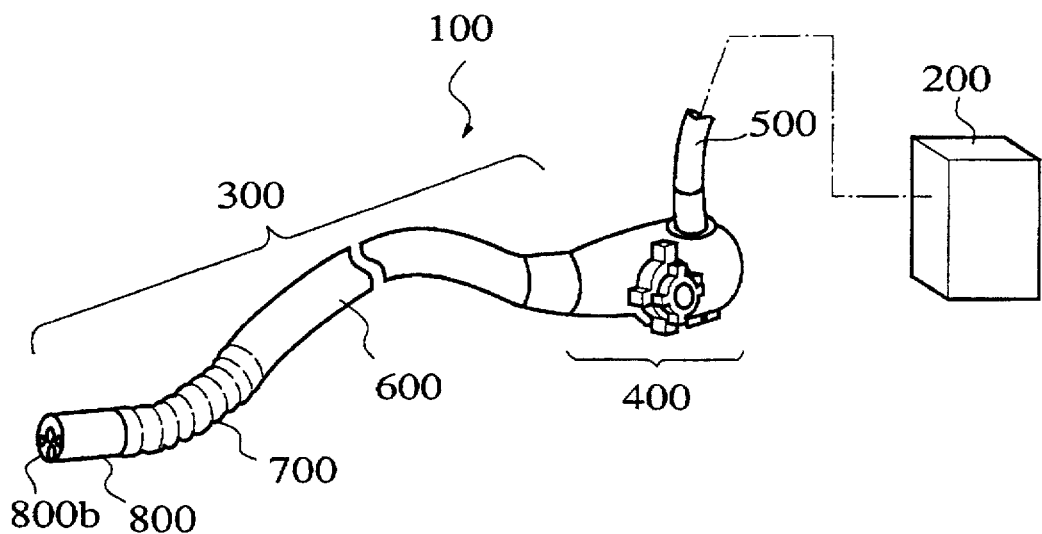
FIG. 7 is a perspective view showing an essential part of an endoscopic apparatus according to an embodiment of the present invention.

FIG. 7 shows an endoscopic apparatus. The apparatus includes an endoscope 100 to be inserted into a body cavity and a main unit 200 connected to the endoscope 100. The main unit 200 includes a control system, an optical system, an image processing system, a display system, etc., to drive the endoscope 100, obtain images, and display the images.

The endoscope 100 includes an insert 800 to be inserted into a body cavity and a controller 400 for externally controlling the insert 300. The controller 400 is connected to the main unit 200 through a universal cord 500. The insert 300 consists of a flexible section 600 connected to the controller 400, a flexible angle section 700 connected to the flexible section 600, and a head 800 connected to an end of the angle section 700.

Figure 8:
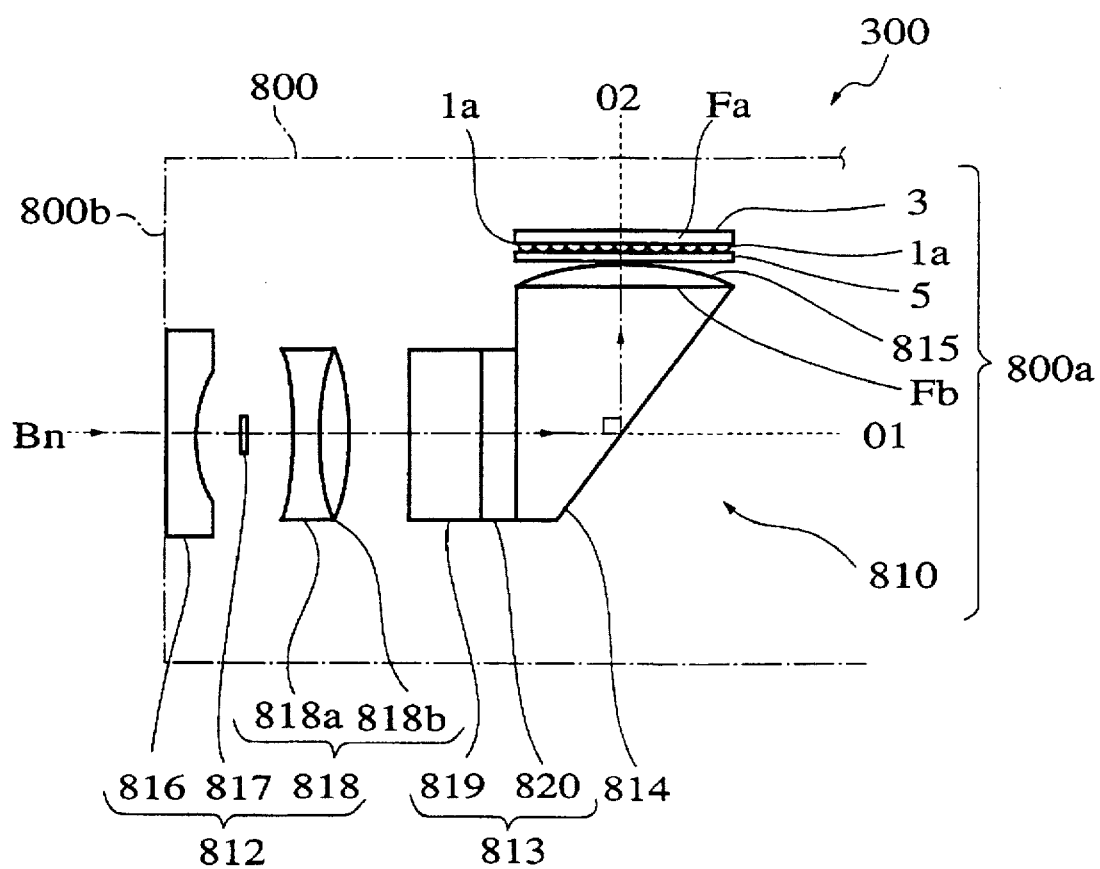
FIG. 8 is a sectional view showing an essential part of an optical system in a head of the endoscopic apparatus.

FIG. 8 shows an optical image pickup system 800a incorporated in the head 800. The image pickup system 800a includes a photosensitive chip 3 having photosensitive elements such as photodiodes corresponding to pixels. An optical system 810 forms an optical image on a photosensitive surface Fa of the photosensitive chip 3.

The photosensitive surface Fa is flat and has a grid of openings corresponding to the photosensitive elements, respectively. A normal to the photosensitive surface Fa is substantially orthogonal to the center axis of the endoscope 100. A grid of microlenses 1a for condensing light are arranged on the photosensitive surface Fa of the photosensitive chip 3. The microlenses 1a correspond to the photosensitive elements, respectively. A glass plate 5 covers the incident surfaces of the microlenses 1a. The glass plate 5 is coaxial to the chip 3. Light Bn is transmittedd through the glass plate 5 and is condensed by the microlenses 1a onto the photosensitive elements on the photosensitive surface Fa.
Fifth Embodiment The optical system 810 has an object lens 812 for passing light Bn from an object, an optical filter 813 for transmitting light of a given wavelength among the light Bn, a prism 814 for changing the path of the light Bn toward the photosensitive surface Fa of the photosensitive chip 3, and a plano-convex lens 815 for making the light Bn from the prism 814 substantially in parallel with a normal to the photosensitive surface Fa depending on the incident angle of the light Bn.

The object lens 812 consists of a concave lens 816 arranged in parallel with an end face 800b of the head 800, a diaphragm 817 for adjusting the quantity of light, arranged on the emission side of and coaxial to the concave lens 816, and an achromatic lens 818 for correcting chromatic aberration. The achromatic lens 818 consists of a concave lens 818a and a convex lens 818b, to correct a deviation in image positions due to different wavelengths in the light Bn.

The optical filter 813 consists of a crystal filter 819 coaxial to the object lens 812 and a color correction filter 820 joined with an emission surface of the crystal filter 819. The crystal filter 819 removes color pseudo signals produced by the photosensitive chip 3. The color correction filter 820 removes infrared rays contained in the light Bn transmitted through the crystal filter 819. When the endoscopic apparatus is used for an infrared laser treatment, infrared rays from an infrared laser may saturate image signals in the chip 3. If this happens, endoscopic images displayed will be invisible. The color correction filter 820 prevents this problem.

The prism 814 is necessary because the photosensitive chip 3 is orthogonal to the axis of the endoscope. An incident surface of the prism 814 is joined with an emission surface of the color correction filter 820, and an emission surface Fb of the prism 814 is coaxial to the photosensitive surface Fa of the chip 3. The prism 814 changes the path of the light Bn along the axis of the color correction filter 820 into one that goes to the photosensitive surface Fa of the chip 3.

The plano-convex lens 815 is arranged between the emission surface Fb of the prism 814 and the photosensitive surface Fa of the chip 3. The lens 815 is coaxial to the photosensitive surface Fa. A flat surface of the lens 815 is joined with the emission surface Fb of the prism 814, and a convex surface of the lens 815 faces the glass plate 5. The radius of curvature of the convex surface of the lens 815 is properly determined according to the refractive index of the lens 818 and simulations of ray traces.

Figure 9:
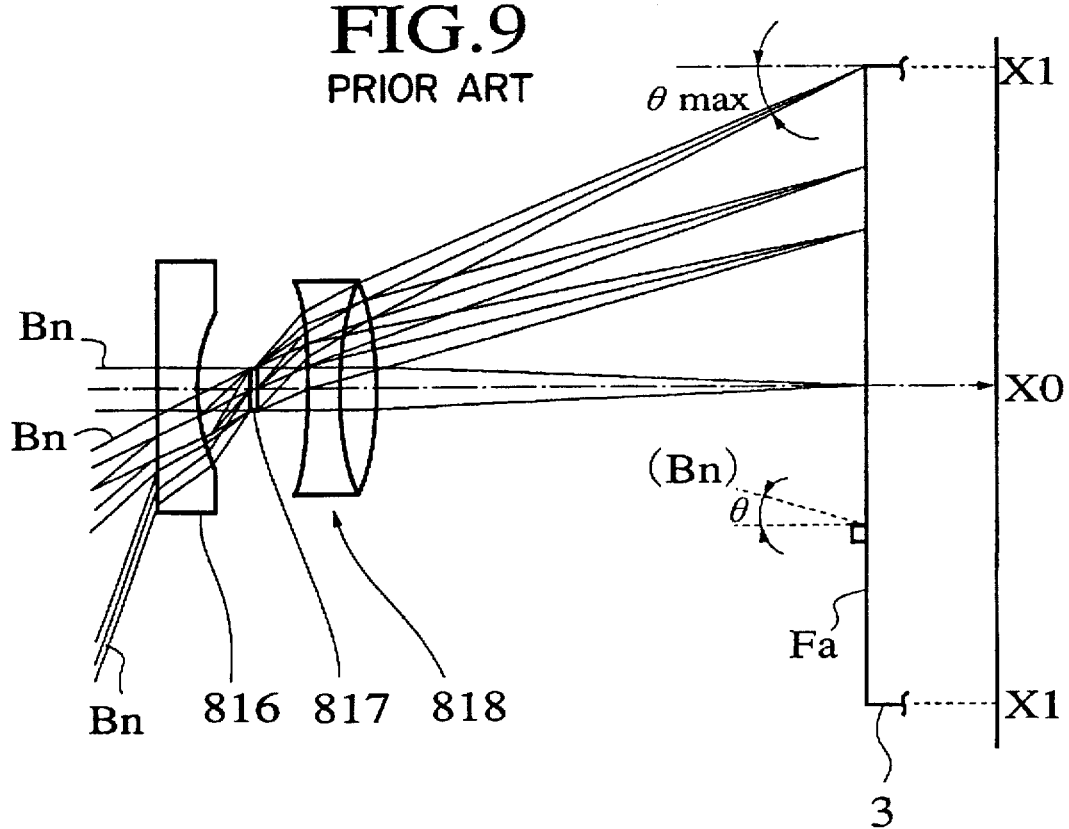
FIG. 9 shows traces of light in an image pickup device with no plano-convex lens.
Figure 10:
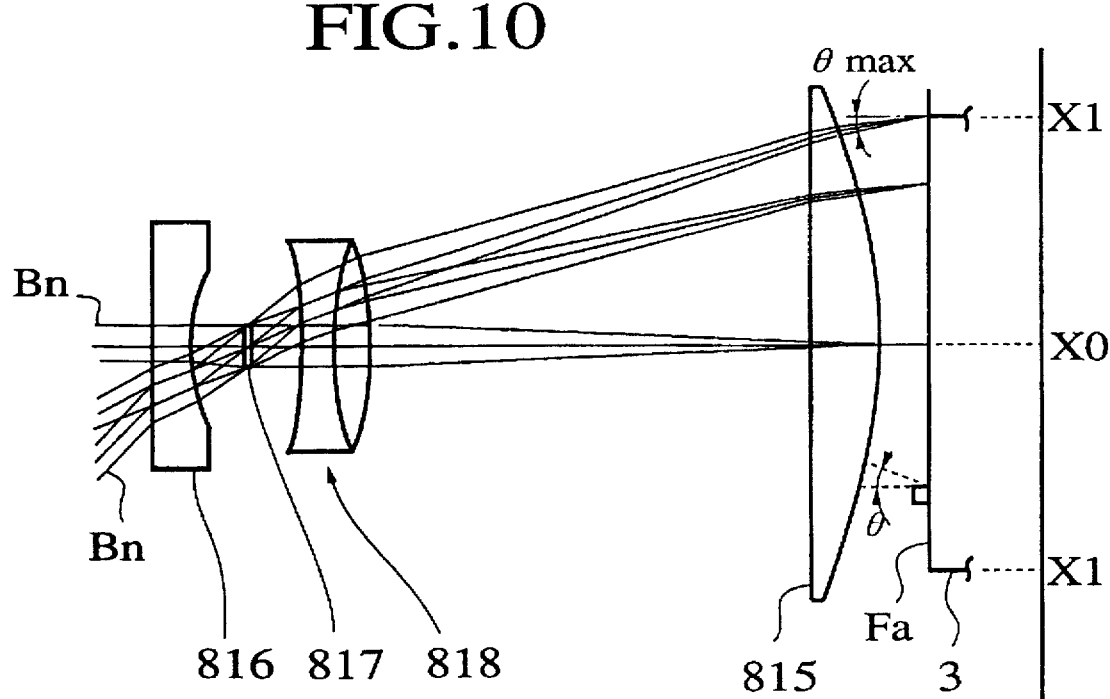
FIG. 10 shows traces of light in an image pickup device with a plano-convex lens.

FIGS. 9 and 10 show traces of light for explaining the plano-convex lens 815.

These traces are results of simulations carried out on models. Each model consists of an object lens 812 and a photosensitive chip 3 coaxial to the object lens 812.

The simulations are carried out by changing the direction of light Bn made incident to the optical lens 812. An incident angle θ of the light Bn to a photosensitive surface Fa of the photosensitive chip 3 is calculated whenever the direction of the light Bn is changed. If the incident angle θ exceeds a proper value θ a, reflection on the photosensitive surface Fa deteriorates photosensitivity due to the characteristics of the chip (CCD) 3. When the chip 3 has microlenses, a proper incident angle is θ b which is about six degrees and is smaller than θ a. If the incident angle θ is greater than the proper angle θ b, the oblique incident deteriorates photosensitivity.

FIG. 9 shows the prior art with no plano-convex lens 815 between the object lens 812 and the photosensitive chip 3.

In FIG. 9, the incident angle θ of the light Bn is minimum at the center X0 of the photosensitive surface Fa, gradually increases as the light Bn approaches an edge of the surface Fa, and reaches a maximum value θ max of about 25 degrees at an edge X1 of the surface Fa. The θ max is far greater than the proper value θ b of about six degrees for a photosensitive chip with microlenses. Only an area around the center X0 satisfies the proper incident angle θ b. The θ max of 25 degrees is also far greater than the proper angle θ a for a photosensitive chip with no microlenses.

FIG. 10 shows the present invention employing the plano-convex lens 815.

In FIG. 10, the maximum incident angle θ max of the light Bn at each edge X1 of the photosensitive surface Fa is about six degrees. This angle is substantially equal to the proper angle θ b and is about ¼ of the maximum incident angle θ of the prior art of FIG. 9. Accordingly, the present invention realizes satisfactory incident angles on the whole of the photosensitive surface Fa of the chip 3 without microlenses (the larger proper angle of θ a) or with microlenses (the smaller proper angle of θ b). The refractive index and curvature of the plano-convex lens 815 are optionally set according to a required maximum incident angle θ max.

According to these simulations and the positions of the photosensitive chip 3 and optical system 810 in the head 800, the refractive index and curvature of the plano-convex lens 815 are set to provide a proper incident angle for incident light Bn.

In FIG. 8, the plano-convex lens 815 of the present invention changes the path of the light Bn emanating from the prism 814 of the optical system 810, so that the light Bn may substantially vertically enter the photosensitive surface Fa of the photosensitive chip 3 through the glass plate 5.

Namely, the vertically adjusted light is transmitted through the glass plate 5 and microlenses 1a, which condense the light into the openings of the photosensitive elements on the surface Fa. The light never obliquely enters the photosensitive chip 3, and therefore, photosensitivity will never be deteriorated. Even if light that may have an incident angle greater than the allowable incident angle of the microlenses arrives, the lens 815 changes the path of the light just before it enters the microlenses, to fully utilize the function of the microlenses. This results in improving the resolution of endoscopic images displayed and the efficiency of endoscopic diagnosis.

The plano-convex lens 815 lets the light Bn enter the photosensitive chip 3 at proper incident angles, so that the diameter of the object lens arranged on the incident side of the lens 815 may be reduced to reduce the diameter of the endoscope 100. This results in reducing pain to a patient during an endoscopic examination.

Although the photosensitive chip 3 is arranged orthogonal to the axis of the endoscope, this configuration does not limit the present invention. For example, the photosensitive chip 3 may be arranged as shown in FIGS. 9 and 10.

The structure of FIG. 8 may employ a reflector instead of the prism 814.

Sixth and seventh embodiments will be explained with reference to FIGS. 11 and 12.

These embodiments partly modify the image pickup system 800a of FIG. 8. The microlenses 1a of the preceding embodiments are not shown in FIGS. 11 and 12. The same or identical parts as those of the preceding embodiments are represented with like reference marks, and they are not explained again.

Sixth Embodiment

Figure 11:
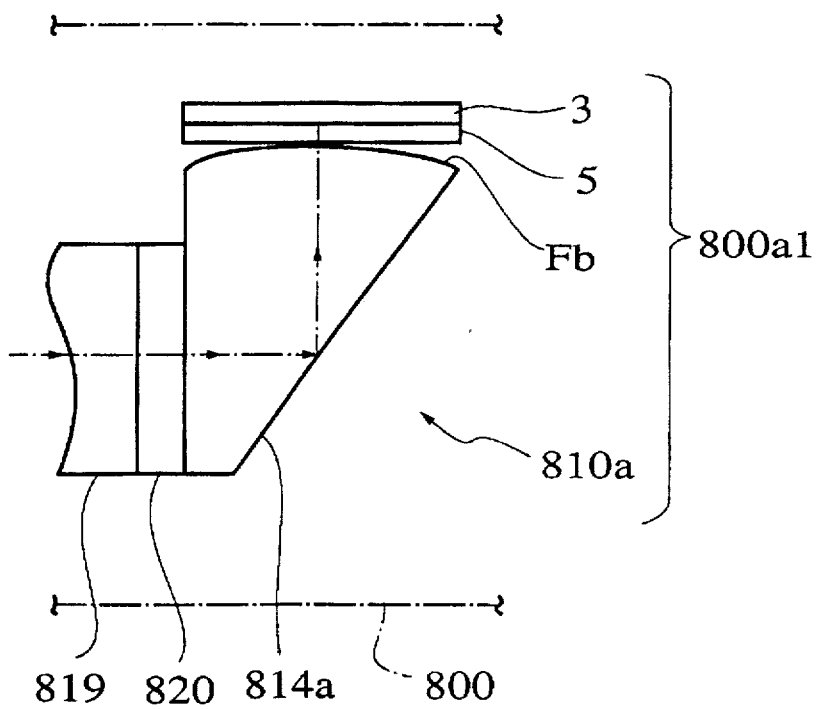
FIG. 11 is a sectional view showing an essential part of an endoscopic apparatus according to a sixth embodiment of the present invention.

FIG. 11 shows an image pickup system 800a1 according to the sixth embodiment. This embodiment shapes an emission surface of a prism 814a in an optical system 810a into a convex surface and uses it as the plano-convex lens 815 of FIG. 8. The curvature of the convex surface is equal to that of the lens 815. The other parts of the sixth embodiment are the same as those of the embodiment of FIG. 8.

In this way, the emission surface Fb of the prism 814a of the sixth embodiment provides the same function as the plano-convex lens 815. Accordingly, the sixth embodiment not only provides the same effect as the fifth embodiment but also simplifies the structure of a head of an endoscope because it has no plano-convex lens.

Seventh Embodiment

Figure 12:
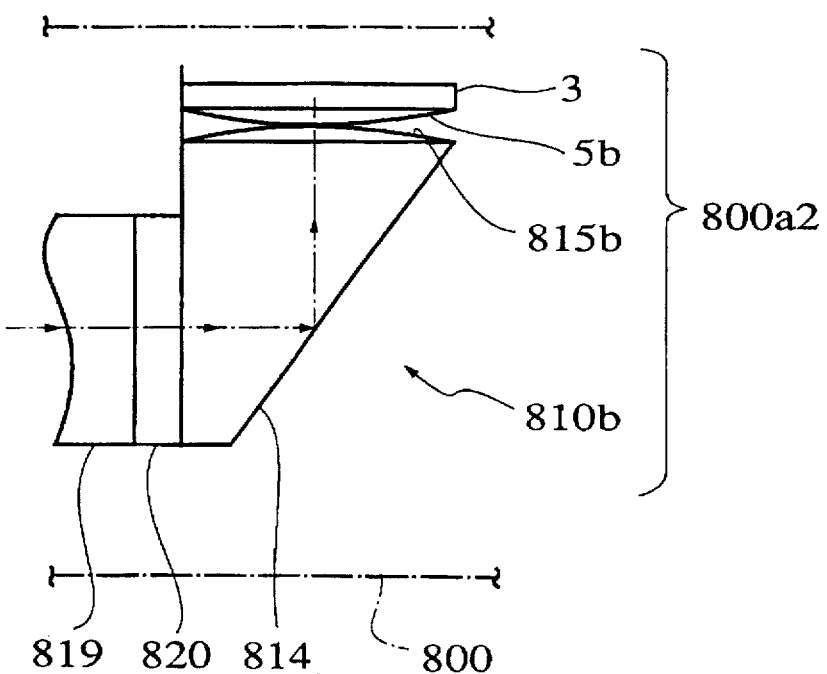
FIG. 12 is a sectional view showing an essential part of an endoscopic apparatus according to a seventh embodiment of the present invention.

FIG. 12 shows an image pickup system 800a2 according to the seventh embodiment. This embodiment employs a glass cover 5b having a convex incident surface, in addition to the structure of the sixth embodiment. Namely, this embodiment has two plano-convex lenses between a photosensitive chip 3 and a prism 814. The radius of curvature of each of the two lenses is larger than that of the lens of the single-plano-convex-lens structure. The other parts of the seventh embodiment are the same as those of the embodiment of FIG. 8. The plano-convex lens 815b on the prism 814 may be formed by shaping an emission surface Fb of the prism 814 into a convex similar to the sixth embodiment.

In this way, the seventh embodiment employs two separate plano-convex lenses, or a glass cover and prism each having a convex surface serving as a plano-convex lens. In each case, the radius of curvature of each of the two plano-convex lenses is larger than that of the plano-convex lens of the sixth embodiment. Accordingly, the seventh embodiment provides the same effect as the sixth embodiment. In addition, the seventh embodiment is capable of reducing a distance between the photosensitive chip 3 and the prism 814 to increase the degree of freedom of designing.

The solid-state image pickup devices according to the present invention mentioned above are applicable not only to endoscopic apparatuses but also to small-sized image pickup apparatuses that are limited in the sizes and positions of an optical system and a photosensitive chip.

It should be understood that many modifications and adaptations of the invention will become apparent to those skilled in the art and it is intended to encompass such obvious modifications and changes in the scope of the claims appended hereto.

What is claimed is:

1. An endoscopic apparatus having an endoscope with a head, the head comprising:

an optical system having an object lens and a prism, said object lens being coaxial with the endoscope, said prism having an incident surface for receipt of light from said object lens and an emission surface;

a solid-state image pickup device having microlenses and a photosensitive chip composed of photosensitive elements, said microlenses adapted to condense light onto said photosensitive elements, an imaginary axis normal to said solid-state image pickup device being orthogonal to an axis of the endoscope, said emission surface of said prism being coaxial to said solid-state image pickup device; and a plano-convex lens arranged coaxial to said solid-state image pickup device, said plano-convex lens having a flat surface joined to said emission surface of said prism, said plano-convex lens adapted to change a path of light from said optical system to said microlenses depending upon an incident angle of light transmitted by said optical system to said microlenses.

2. An endoscopic apparatus having an endoscope with a head, the head comprising:

an optical system having an object lens and a prism, said object lens being coaxial with the endoscope, said prism having an incident surface for receipt of light from said object lens and a curved emission surface;

a solid-state image pickup device having microlenses and a photosensitive chip composed of photosensitive elements, said microlenses adapted to condense light onto said photosensitive elements, an imaginary axis normal to said solid-state image pickup device being orthogonal to an axis of the endoscope, said curved emission surface of said prism being coaxial to said solid-state image pickup device; and a lens having at least one convex surface, said lens arranged coaxial to said solid-state image pickup device, said lens and said curved emission surface of said prism adapted to change a path of light from said optical system to said microlenses depending upon an incident angle of light transmitted by said optical system to said microlenses.

3. An endoscopic apparatus having an endoscope with a head, the head comprising:

an optical system having an object lens coaxial to the endoscope;

a solid-state image pickup device having microlenses and a photosensitive chip composed of photosensitive elements, said microlenses adapted to condense light onto said photosensitive elements;

a glass cover overlying said microlenses of said solid-state image pickup device, said glass cover having a curved incident surface;

a plano-convex lens being arranged coaxial to said solid-state image pickup device, said plano-convex lens and said curved incident surface of said glass cover adapted to change a path of light from said optical system to said microlenses depending upon an incident angle of light transmitted by said optical system to said microlenses.

4. The endoscopic apparatus according to claim 3, wherein:

said photosensitive elements form a photosensitive surface of said solid-state image pickup device, an imaginary axis normal to said photosensitive surface is orthogonal to the axis of the endoscope;

said optical system further comprises a prism having an incident surface for receiving light from said object lens and an emission surface coaxial to said photosensitive surface; and said plano-convex lens has a flat surface that is joined with said emission surface of said prism.

5. An endoscopic apparatus having an endoscope with a head, the head comprising:

an optical system having an object lens and a prism, said object lens being coaxial to the endoscope, said prism having an incident surface for receiving light from said object lens and a curved emission surface;

a solid-state image pickup device having microlenses and a photosensitive chip composed of photosensitive elements, said microlenses adapted to condense light onto said photosensitive elements, said photosensitive elements forming a photosensitive surface coaxial with said curved emission surface of said prism, an imaginary axis normal to said solid-state image pickup device being orthogonal to an axis of the endoscope; and a glass cover provided on said photosensitive surface and having a curved incident surface;

said curved emission surface of said prism and said curved incident surface of said glass cover adapted to change a path of light from said optical system to said microlenses depending upon an incident angle of light transmitted by said optical system to said microlenses.

6. An endoscopic apparatus having an endoscope with a head, the head comprising:

an optical system having an object lens and a prism, said object lens and said prism each having a light emission surface, said object lens being oriented coaxial to the endoscope and said prism being provided opposite said light emission surface of said object lens;

a solid-state image pickup device having a photosensitive chip composed of photosensitive elements which receive light from said optical system; and a plano-convex lens oriented coaxial to said solid-state image pickup device, said plano-convex lens having a flat surface joined to said light emission surface of said prism, said plano-convex lens adapted to change a path of light transmitted by said object lens and said prism and to reduce an incident angle of the transmitted light.

7. An endoscopic apparatus according to claim 6, wherein each of said photosensitive elements of solid-state image pickup device comprises a microlens for condensing light.

8. An endoscopic apparatus according to claim 6, wherein said object lens has a diameter smaller than an imaginary diagonal line across an image pick up area of said solid-state image pickup device.

9. An endoscopic apparatus having an endoscope with a head, the head comprising:

an optical system having an object lens and a prism, said object lens and said prism each having a light emission surface, said object lens oriented coaxial to the endoscope and said prism provided opposite said light emission surface of said object lens; and a solid-state image pickup device having a photosensitive chip composed of photosensitive elements which receive light from said optical system, said light emission surface of said prism being convex and oriented coaxial to said solid-state image pickup device, said light emission surface of said prism adapted to reduce an incident angle of light transmitted by said object lens.

10. An endoscopic apparatus according to claim 9, wherein each of said photosensitive elements of solid-state image pickup device comprises a microlens for condensing light.

11. An endoscopic apparatus according to claim 9, wherein said object lens has a diameter smaller than an imaginary diagonal line across an image pick up area of said solid-state image pickup device.

12. An endoscopic apparatus having an endoscope with a head, the head comprising:

an optical system having an object lens oriented coaxial to the endoscope;

a solid-state image pickup device having a photosensitive chip composed of photosensitive elements which receive light from said the optical system, said photosensitive elements forming a photosensitive surface;

a plano-convex lens oriented coaxial to said solid-state image pickup device; and a glass cover joined to said photosensitive surface of said solid-state image pickup device, said glass cover having a curved incident surface facing away from said photosensitive surface, said plano-convex lens and said glass cover adapted to reduce an incident angle of light transmitted by said object lens.

13. An endoscopic apparatus according to claim 12, wherein each of said photosensitive elements of solid-state image pickup device comprises a microlens for condensing light.

14. An endoscopic apparatus according to claim 12, wherein said object lens has a diameter smaller than an imaginary diagonal line across an image pick up area of said solid-state image pickup device.

15. An endoscopic apparatus having an endoscope with a head, the head comprising:

an optical system having an object lens and a prism, said object lens and said prism each having a light emission surface, said object lens oriented coaxial to the endoscope and said prism provided opposite said light emission surface of said object lens;

a solid-state image pickup device having a photosensitive chip composed of photosensitive elements which receive light from said optical system, said photosensitive elements forming a photosensitive surface;

a plano-convex lens oriented coaxial to said solid-state image pickup device, said plano-convex lens having a flat surface joined to said light emission surface of said prism; and a glass cover joined to said photosensitive surface of said solid-state image pickup device, said glass cover having a curved incident surface facing away from said photosensitive surface, said plano-convex lens and said curved incident surface of said glass cover adapted to change a path of light transmitted by said object lens and to reduce an incident angle of the transmitted light.

16. An endoscopic apparatus according to claim 15, wherein each of said photosensitive elements of solid-state image pickup device comprises a microlens for condensing light.

17. An endoscopic apparatus according to claim 15, wherein said object lens has a diameter smaller than an imaginary diagonal line across an image pick up area of said solid-state image pickup device.

18. An endoscopic apparatus having an endoscope with a head, the head comprising:

an optical system having an object lens and a prism, said object lens and said prism each having a light emission surface, said object lens being oriented coaxial to the endoscope and said prism being provided opposite said light emission surface of said object lens, said light emission surface of said prism being convex;

a solid-state image pickup device having a photosensitive chip composed of photosensitive elements which receive light from said optical system, said photosensitive elements forming a photosensitive surface; and a glass cover joined to said photosensitive surface of said solid-state image pickup device, said glass cover having a curved incident surface facing away from said photosensitive surface and joined to said light emission surface of said prism, said curved incident surface of said glass cover and said light emission surface of said prism adapted to change a path of light transmitted by said object lens and to reduce an incident angle of the transmitted light.

19. An endoscopic apparatus according to claim 18, wherein each of said photosensitive elements of solid-state image pickup device comprises a microlens for condensing light.

20. An endoscopic apparatus according to claim 18, wherein said object lens has a diameter smaller than an imaginary diagonal line across an image pick up area of said solid-state image pickup device.

* * * * *